United States Patent [19]

Eller et al.

[11] Patent Number: 5,786,510

[45] Date of Patent: Jul. 28, 1998

[54] PREPARATION OF AMINES FROM OLEFINS OVER CRYSTALLINE OXIDES BASED ON ALUMINUM PHOSPHATES AND HAVING FAUJASITE STRUCTURE

[75] Inventors: Karsten Eller, Ludwigshafen; Rudolf Kummer, Frankenthal; Peter Stops, Altrip, all of Germany

[73] Assignee: BASF Aktiengesellschaft, Ludwigshafen, Germany

[21] Appl. No.: 784,772

[22] Filed: Jan. 16, 1997

[30] Foreign Application Priority Data

Jan. 17, 1996 [DE] Germany .................. 196 01 409.3

[51] Int. Cl.⁶ .................................................. C07C 209/02
[52] U.S. Cl. .................................................. 504/485
[58] Field of Search .................................................. 564/485

[56] References Cited

U.S. PATENT DOCUMENTS

| | | | |
|---|---|---|---|
| 4,375,002 | 2/1983 | Peterson et al. | 564/445 |
| 4,536,602 | 8/1985 | Deeba | 564/485 |
| 5,648,546 | 7/1997 | Bergfeld et al. | 564/485 |

FOREIGN PATENT DOCUMENTS

| | | |
|---|---|---|
| 2092964 | 3/1993 | Canada . |
| 101 921 | 3/1984 | European Pat. Off. . |
| 133 938 | 7/1984 | European Pat. Off. . |
| 305 564 | 3/1989 | European Pat. Off. . |
| 431 451 | 11/1990 | European Pat. Off. . |
| 752 409 | 6/1996 | European Pat. Off. . |
| 42 06 992 | 3/1992 | Germany . |

OTHER PUBLICATIONS

Brunet et al., *J. Mol. Catal.*, vol. 49 (1989), pp. 235–259.
Kiyora et al., *Chemical Abstracts*, vol. 18 (1993), p. 704, No. 6620d (English abstract of JP-A-04/139,156).
Database WPI Week 9513, Derwent Publications Ltd., AN 95-096945 (English abstract of RU 2015959 C) (Jan. 1995).

*Primary Examiner*—Brian M. Burn

*Attorney, Agent, or Firm*—Keil & Weinkauf

[57] ABSTRACT

A process for the preparation of amines of the general formula I

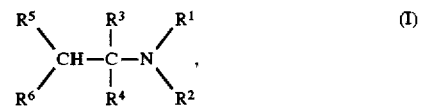

in which $R^1, R^2, R^3, R^4, R^5$, and $R^6$ denote hydrogen, $C_1$–$C_{20}$ alkyl, $C_2$–$C_{20}$ alkynyl, $C_3$–$C_{20}$ cycloalkyl, $C_4$–$C_{20}$ alkylcycloalkyl, $C_4$–$C_{20}$ cycloalkylalkyl, aryl, $C_7$–$C_{20}$ alkylaryl or $C_7$–$C_{20}$ aralkyl, $R^1$ and $R^2$ together denote a saturated or unsaturated $C_3$–$C_9$ alkylene dichain and $R^3$ or $R^5$ denotes $C_{21}$–$C_{200}$ alkyl, $C_{21}$–$C_{200}$ alkenyl or they together form a $C_2$–$C_{12}$ alkylene dichain.

by the reaction of olefins of the general formula II

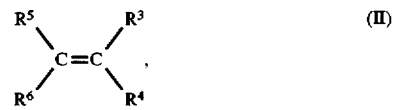

in which $R^3$, $R^4$, $R^5$ and $R^6$ have the aforementioned meanings, with ammonia or primary or secondary amines of the general formula III

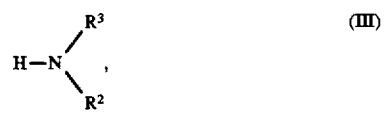

in which $R^1$ and $R^2$ have the aforementioned meanings, at temperatures ranging from 200° to 350° C. and pressures of from 100 to 300 bar in the presence of a heterogeneous catalyst, wherein the heterogeneous catalysts used are crystalline oxides based on aluminum phosphates and having faujasite structure.

13 Claims, No Drawings

PREPARATION OF AMINES FROM OLEFINS OVER CRYSTALLINE OXIDES BASED ON ALUMINUM PHOSPHATES AND HAVING FAUJASITE STRUCTURE

The present invention relates to a process for the preparation of amines by the reaction of ammonia or primary or secondary amines with olefins at elevated temperatures and pressures in the presence of crystalline oxides based on aluminum phosphates and having faujasite structure.

An overview of the methods of aminating olefins is given in "Functionalisation of Alkenes: Catalytic Amination of Monoolefins", J. J. Brunet et al J. Mol. Catal., 49 (1989), pp 235 to 259.

Basically there are two catalysis mechanisms. The olefin is coordinated via a metal complex. This activated species can be attacked by the nucleophilic amine and form a more highly aminated product. The amine can be chemisorbed at acid centers or at metal centers (via metal amides) and, thus activated, can be caused to react with the olefin.

Well-suited catalysts are zeolites. They are distinguished by a large number of catalytically active centers, combined with a large surface area. The zeolites described differ in type and requisite post-treatment (eg thermal treatment, dealumination, acid treatment, metal ion exchange, etc). Examples thereof may be found in U.S. Pat. No. 4,375,002, U.S. Pat. No. 4,536,602, EP-A 305,564, EP-A 101,921, and DE-A 4,206,992.

EP-A 133,938, EP-A 431,451 and EP-A 132,736 reveal processes in which boron, gallium, aluminum, and iron silicate zeolites are used for the preparation of amines from olefins and reference is made to the possibility of doping these zeolites with alkali metals, alkaline earth metals, and transition metals.

CA-A 2,092,964 reveals a process for the preparation of amines from olefins, in which β-zeolites, which are defined as being crystalline aluminum silicates of specific composition and having a pore size of greater than 5 Å, are used. Metal-modified or halogen-modified β-zeolites are preferably used.

JP-A 04/139156 discloses a process for the preparation of tertiary amines from olefins over silicon-aluminum phosphates or metal-silicon-aluminum phosphates.

However, the use of diisopropylamine as a template for the synthesis of crystalline SAGO's or MeAPO's usually leads to crystalline structures having a relatively narrow distribution of pore diameters (Handbook of Molecular Sieves, Van Nostrand Reinhold, N.Y. 1992 578), eg of the types CoAPO-11 (AEL), CoAPO-34 (CHA) or MgAPSO-39 (ATN). Only SAPO-11 (AFI) possesses pore diameters into which, eg, isobutene as the smallest of the olefins can diffuse to react with ammonia to form the tertiary amine.

All processes for the synthesis of amines from olefins over these catalysts are marked by a small amine yield or small space-time yield, or lead to rapid deactivation of the catalysts.

It is thus an object of the present invention to overcome these drawbacks.

We have now found that, surprisingly, the use of crystalline oxides based on aluminum phosphates and having faujasite structure can overcome the aforementioned disadvantages. These catalysts have hitherto been considered to be unusable, since they change to amorphous material in air. However, we have been able to make use of them for the desired purpose by effecting calcination of the template-containing crystals directly in the amination reactor without them undergoing transformation to the less active amorphous aluminum phosphates.

Accordingly we have found a novel and improved process for the preparation of amines of the general formula I

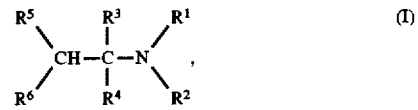

in which $R^1$, $R^2$, $R^3$, $R^4$, $R^5$, and $R^6$ denote hydrogen, $C_1$–$C_{20}$ alkyl, $C_2$–$C_{20}$ alkenyl, $C_2$–$C_{20}$ alkynyl, $C_3$–$C_{20}$ cycloalkyl, $C_4$–$C_{20}$ alkylcycloalkyl, $C_4$–$C_{20}$ cycloalkylalkyl, aryl, $C_7$–$C_{20}$ alkylaryl or $C_7$–$C_{20}$ aralkyl, $R^1$ and $R^2$ together denote a saturated or unsaturated $C_3$–$C_9$ alkylene dichain and $R^3$ or $R^5$ denotes $C_{21}$–$C_{200}$ alkyl, $C_{21}$–$C_{200}$ alkenyl or they together form a $C_2$–$C_{12}$ alkylene dichain, by the reaction of olefins of the general formula II

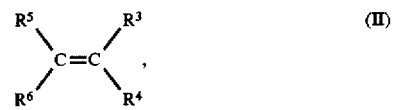

in which $R^3$, $R^4$, $R^5$, and $R^6$ have the aforementioned meanings, with ammonia or primary or secondary amines of the general formula III

in which $R^1$ and $R^2$ have the aforementioned meanings, at temperatures ranging from 200° to 350° C. and pressures of from 100 to 300 bar in the presence of a heterogeneous catalyst, wherein the heterogeneous catalyst used is a crystalline oxide based on aluminum phosphates and having faujasite structure.

The process of the invention can be carries out as follows:

The olefin II and ammonia or the primary or secondary amine III can be caused to react at temperatures ranging from 200° to 350° C., preferably from 220° to 330° C. and more preferably from 230° to 320° C. and pressures of from 100 to 300 bar, preferably from 120 to 300 bar and more preferably form 140 to 290 bar in the presence of crystalline oxides based on aluminum phosphates and having faujasite structure as catalyst eg in an autoclave, and preferably the amine obtained can be separated and the unconverted starting materials recycles.

The present process is distinguished by very good yields at a high degree of selectivity and high space-time yields. Moreover deactivation of the catalyst has been repressed.

The process of the invention is distinguished by the fact that a high selectivity toward the desired reaction product is achieved even with low excess of ammonia or amine and dimerization and/or oligomerization of the olefin used is avoided.

One embodiment of this process consists in that ammonia and/or amines III mixed with the olefin II in a molar ratio of from 1:1 to 5:1 are fed to a fixed bed reactor and caused to react under a pressure of from 100 to 300 bar and at a temperature of from 200° to 350° C. in the gas phase or in a supercritical state.

The desired product can be obtained from the effluent by known methods such as distillation or extraction, and purified to the desired extent if necessary be means of further separations. The unconverted starting materials are usually preferably recycled to the reactor.

The starting materials used can be mono- or polyunsaturated olefins II, particularly those containing from 2 to 10 carbon atoms or mixtures thereof, and polyolefins. On account of their low degree of actual polymerization proneness monoolefins are more suitable than diolefins and polyolefins, but these can be converted with an equal degree of selectivity by using higher excesses of ammonia or amine. The point of equilibrium and thus the degree of conversion to the desired amine is very much dependent on the reaction pressure used. High pressure favors the addition product, but a pressure range up to 300 bar is generally the optimum for technical and economical reasons. The selectivity of the reaction is influenced in addition to factors such as excess of ammonia or amine and the catalyst used—to a great extent by the temperature. Although the reaction velocity of the addition reaction shows a marked increase with increasing temperature, competitive cracking and recombining reactions of the olefin are simultaneously promoted. Moreover a temperature increase is not advantageous from a thermodynamic point of view. The optimum temperature with regard to conversion and selectivity is governed by the nature of the olefin, the amine used and the catalyst and is mostly in a range of from 200° to 350° C.

Suitable catalysts for the amination of olefins are crystalline oxides based on aluminum phosphates and having faujasite structure. Such materials are described, for example, in U.S. Pat. No. 4,440,871 as SAPO-37, or in EP-A 158.976 as FCAPO-37, or in EP-158,977 as MeAPO-37. A discussion on the structural relationships of SAPO's, AlPO's, MeAPO's, and MeAPSO's may be found in, eg, Stud. Surf. Catal. 37 (1987), pages 13 to 27. The AlPO's used in the present invention contain aluminum and phosphorus in a ratio greater than 1:1, whilst in the SAPO's some of the phosphorus and/or some of both phosphorus and aluminum is replaced by silicon. In the MeAPO's various metals are present, such as Li, B, Be, Mg, Ti, Mn, Fe, Co, An, Ga, Ge, and As, in addition to aluminum and phosphorus, whilst the MeAPSO's additionally containg silicon. The negative charge of the $Me_aAl_bP_cSi_dO_o$ lattice is compensated by cations.

The aluminum-oxide-based crystalline oxides and having faujasite structure used in the invention can be shaped as such, or alternatively they can be mixed with a binding agent in a ratio of from 98:2 to 40:60 wt % to form extrudates or pellets. Suitable binding agents are various aluminum oxides, preferably boehmite, amorphous aluminum silicates showing a $SiO_2/Al_2O_3$ ratio of from 25:75 to 95:5, silicon dioxide, preferably microdispersed $SiO_2$, mixtures of microdispersed $SiO_2$ and microdispersed $Al_2O_3$, microdispersed $TiO_2$, and also clays. Following shaping, the extrudates or molded articles are advantageously dried at 110° C. over a period of 16 hours and calcined at from 200° to 500° C. over a period of 2 hours, the calcination being preferably carried out in situ in the amination reactor.

To increase the selectivity, the on-stream time and the number of possible regenerations, various modifications can be performed on the aluminum phosphate-based crystalline oxides and having faujasite structure used in the invention.

One modification of the catalysts consists in doping the aluminum phosphate-based crystalline oxides having faujasite structure with alkali metals such as Na and K, alkaline earth metals such as Ca, Mg, earth metals such as Tl, transition metals such as Ti, Zr, Mn, Fe, Mo, Cu, Zn, Cr, noble metals, and/or rare earth metals such as La, Ce, Y.

The catalysts can be used in the form of extrudates having diameters of, eg, from 1 to 4 mm or as pellets having a diameter of, say, from 3 to 5 mm, for the amination of the olefins.

From the catalyst shaped, eg, by extrusion there can be obtained, by milling and sifting, a fluid bed material showing a particle size of from 0.1 to 0.8 mm.

The substituents $R^1$, $R^2$, $R^3$, $R^4$, $R^5$, and $R^6$ in the compounds I, II and III have the following meanings:

$R^1$, $R^2$, $R^3$, $R^4$, $R^5$, and $R^6$ hydrogen, $C_1$–$C_{20}$ alkyl, preferably $C_1$–$C_{12}$ alkyl and more preferably $C_1$–$C_8$ alkyl such as methyl, ethyl, n-propyl, isopropyl, n-butyl, isobutyl, sec-butyl, tert-Butyl, n-pentyl, isopentyl, n-hexyl, isohexyl, n-heptyl, isoheptyl, n-octyl, and isooctyl, $C_2$–$C_{20}$ alkenyl, preferably $C_2$–$C_{12}$ alkenyl and more preferably $C_2$–$C_8$ alkenyl such as vinyl and allyl, $C_2$–$C_{20}$ alkynyl, preferably $C_2$–$C_8$ alkynyl and more preferably $C_2H$ and propargyl, $C_3$–$C_{20}$ cycloalkyl, preferably $C_3$–$C_{12}$ cycloalkyl and more preferably $C_5$–$C_8$ cycloalkyl such as cyclopentyl, cyclohexyl, cycloheptyl, and cyclooctyl, $C_4$–$C_{20}$ alkylcycloalkyl, preferably $C_4$–$C_{12}$ alkylcycloalkyl and more preferably $C_5$–$C_{10}$ alkylcycloalkyl, $C_4$–$C_{20}$ cycloalkylalkyl, preferably $C_4$–$C_{12}$ cycloalkylalkyl and more preferably $C_5$–$C_{10}$ cycloalkylalkyl, aryl such as phenyl, 1-naphthyl, and 2-naphthyl, preferably phenyl, $C_7$–$C_{20}$ alkylaryl, preferably $C_7$–$C_{18}$ alkylaryl and more preferably $C_7$–$C_{12}$ alkylphenyl such as 2-methylphenyl, 3-methylphenyl, 4-methylphenyl, 2-ethylphenyl, 3-ethylphenyl, and 4-ethylphenyl, $C_7$–$C_{20}$ aralkyl, preferably $C_7$–$C_{18}$ aralkyl and more preferably $C_7$–$C_{12}$ phenalkyl such as phenylmethyl, 1-phenylethyl, 2-phenylethyl, $R^1$ and $R^2$ together form a saturated or unsaturated $C_3$–$C_9$ alkylene dichain, preferably —$(CH_2)_4$—, —$(CH_2)_5$—, —$(CH_2)_7$—and —CH=CH—CH=CH—, $R^3$ or $R^5$ $C_{21}$–$C_{200}$ alkyl, preferably $C_{40}$–$C_{200}$ alkyl such as polybutyl, polyisobutyl, polypropyl, polyisopropyl, and polyethyl and more preferably polybutyl and polyisobutyl, $C_{21}$–$C_{200}$ alkenyl, preferably $C_{40}$–$C_{200}$ alkenyl and more preferably $C_{70}$–$C_{170}$ alkenyl, $R^3$ and $R^5$ together form a $C_2$–$C_{12}$ alkylene dichain, preferably a $C_3$–$C_8$ alkylene dichain and more preferably —$(CH_2)_3$—, —$(CH_2)_4$—, —$(CH_2)_5$—, —$(CH_2)_6$— and —$(CH_2)_7$—, particularly —$(CH_2)_3$— and —$(CH_2)_4$—.

EXAMPLES

Catalyst Synthesis

Catalyst A: SAPO-37

Solution A was prepared from 152.5 g of $H_2O$, 138.5 g of 85% strength $H_3PO_4$, and 83 g of Pural® SB (AlOOH sold by Condea) and stirred for 6 hours at room temperature.

Solution B was prepared from 580 g of 40% strength tetrapropylammonium hydroxide solution, 5.5 g of tetramethylammonium hydroxide pentahydrate, and 33.5 g of Aerosil® 200 ($SiO_2$ sold by Degussa) and stirred for 2 hours at room temperature.

Solution B was slowly added to solution A with stirring and the mixture was stirred for 24 hours at room temperature. It was then placed in an autoclave having a capacity of 2 liters and crystallized over a period of 48 hours under autogenous pressure (17 bar). The SAPO-37 formed was removed by centrifugation and then dried at 110° C. over a period of 16 hours. The yield was 84 g of an SAPO-37 shown to be of uniform phase by X-ray diffractometry. 60 g of SAPO-37 were admixed with 40 g of boehmite, 2 g of formic acid, and 3 g of starch, compacted in a kneader and kneaded with the addition of water (75 mL) over a period of 60 minutes. In an extruder 2 mm extrudates were produced using a molding pressure of 50 bar, dried at 110° C. over a period of 16 h. 18 g of these template-containing extrudates (equivalent to 14 g of H-SAPO-37 ) were placed in the reactor in the form of gravel and calcined therein with 20 liters of dry air per hour. The temperature treatment used comprised 2 hours at 350° C., 2 hours at 450° C., and 8 hours at 490° C.

Catalyst B: SAPO-5 (comparative example)

64 g of SAPO-5 were admixed with 54 g of a 30% strength silica sol and 5 g of starch, compacted in a kneader and kneaded with the addition of water (16 mL) over a period of 45 minutes. In an extruder 2 mm extrudates were produced using a molding pressure of 100 bar, dried at 110° C. over a period of 16 h and the calcined at 500° C. over a period of 16 h.

Catalyst C: HY-zeolite (comparative example)

2160 g of NaY were admixed with 1440 g of boehmite and 72 g of formic acid, compacted in a kneader and kneaded with the addition of water (1850 mL) over a period of 60 minutes. In an extruder 2 mm extrudates were produced using a molding pressure of 90 bar, dried at 110° C. over a period of 16 h and then calcined at 500° C. over a period of 16 h.

Catalyst D: Amorphous product of H-SAPO-37 (comparative example)

H-SAPO-37 was obtained from catalyst A by calcination and handled in air. X-ray diffraction patterns showed that the material was now in an amorphous state.

Catalyst E: SAPO-37

Catalyst E was prepared as Catalyst A except that synthesis was carried out in a stirred autoclave having a capacity of 2.5 L. There were obtained 38 g of a well crystallized SAPO-37 powder which was formed into extrudates in a similar manner to Catalyst A and then caclined in situ.

Catalyst F: SAPO-11 (Comparative example)

To 122.7 g of aluminum isopropylate and 15 g of distilled water there were added, with stirring, 69.4 g of 85% strength $H_3PO_4$ in 180 g of distilled water. There were then added 13.6 g of Ludox® AS 40 (40% $SiO_2$) in 20 g of distilled water and 30.4 g of diisopropylamine in 15 g of distilled water, and the mixture was then crystallized in an autoclave for 48 h at 200° C. The resulting SAPO-11 crystals were isolated by filtration, washed and dried over a period of 4 h at 120° C. and calcined over a period of 12 h at 500° C.

Yield: 70 g of pure-phase SAPO-11 (as shown by the X-ray diffraction method).

To 60 g of SAPO-11 there were added 40 g of boehmite and 2 g of formic acid, and the mixture was compacted in a kneader and kneaded over a period of 45 min with the addition of water (53 ml). In an extruder there were formed 2 mm extrudates under an extruding pressure of 70 bar and these were dried over a period of 16 h at 120° C. and calcined over a period of 16 h at 500° C.

Amination Examples

The experiments were carried out in a tubular reactor (internal diameter 6 mm) under isothermal conditions at temperatures ranging from 270° to 300° C. and a pressure of 280 bar using a mixture of isobutene and ammonia in a molar ratio of 1:1.5. The reaction products were analyzed by gas chromatography.

The results are listed in Table 1 and demonstrate that the catalysts used in the present invention give higher yields than the prior catalyst systems SAPO-5, that in the case of the industrially significant higher space velocities greater yields are obtained than with other faujasites selected from aluminum silicates, and that amorphous oxide exhibiting the composition used in the invention also produce lower yields.

TABLE 1

| | | | tert-Butylamine ($NH_3$: $C_4H_8$ = 1.5) | | | | | |
|---|---|---|---|---|---|---|---|---|
| | | | tert-butylamine yield [wt %] | | | | Binder | |
| Catalyst | Pressure [bar] | Temperature [°C.] | WHSV 0.7 [g/g · h] | WHSV 1.5 [g/g · h] | WHSV 3 [g/g · h] | Weight per liter [kg/L] | $Al_2O_3$ [wt %] | $SiO_2$ [wt %] |
| A | 280 | 270 | 17.84 | 11.14 | 7.95 | 0.51 | 40 | 0 |
| A | 280 | 280 | 18.74 | 15.20 | 10.49 | 0.51 | 40 | 0 |
| A | 280 | 300 | 12.94 | | 12.57 | 0.51 | 40 | 0 |
| B | 280 | 270 | 10.31 | 6.31 | 3.54 | 0.65 | 0 | 20 |
| C | 280 | 270 | 19.12 | 11.50 | 6.16 | 0.63 | 40 | 0 |
| D | 280 | 270 | 12.15 | 6.32 | | 0.51 | 40 | 0 |
| E | 280 | 270 | 18.61 | 14.49 | 10.15 | 0.56 | 40 | 0 |
| E | 280 | 280 | 18.71 | 17.11 | 14.43 | 0.56 | 40 | 0 |
| E | 280 | 300 | 13.85 | 13.22 | 13.15 | 0.56 | 40 | 0 |
| F | 280 | 270 | 4.95 | 2.65 | 1.45 | 0.67 | 40 | 0 |

We claim:

1. A process for the preparation of an amine of the formula I

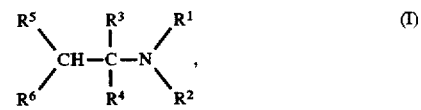

in which $R^1$, $R^2$, $R^3$, $R^4$, $R^5$, and $R^6$ denote hydrogen, $C_1$–$C_{20}$ alkyl, $C_2$–$C_{20}$ alkenyl, $C_2$–$C_{20}$ alkynyl, $C_3$–$C_{20}$ cycloalkyl, $C_4$–$C_{20}$ alkylcycloalkyl, $C_4$–$C_{20}$ cycloalkylalkyl, aryl, $C_7$–$C_{20}$ alkylaryl or $C_7$–$C_{20}$ aralkyl, $R^1$ and $R^2$ together denote a saturated or unsaturated $C_3$–$C_8$ alkylene dichain and $R^3$ or $R^5$ denotes $C_{21}$–$C_{200}$ alkyl, $C_{21}$–$C_{200}$ alkenyl or they together form a $C_2$–$C_{12}$ alkylene dichain.

by the reaction of olefins of the formula II

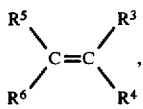

in which $R^3$, $R^4$, $R^5$ and $R^6$ have the aforementioned meanings,
with ammonia or primary of secondary amines of the formula III

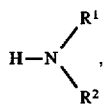

in which $R^1$ and $R^2$ have the aforementioned meanings,
at temperatures ranging from 200° to 350° C. and pressures of from 100 to 300 bar in the presence of a heterogeneous catalyst, wherein the heterogeneous catalyst is a crystalline oxide based on an aluminum phosphate and having faujasite structure, which is produced in the reactor (in situ) by calcination of the template-containing form.

2. A process for the preparation of an amine I as defined in claim 1, wherein the amine I formed is separated and the unconverted starting materials II and III are recycled.

3. A process for the preparation of an amine as defined in claim 1, wherein the olefin II used is isobutene, diisobutene, cyclopentene, cyclohexene, or polyisobutene.

4. A process for the preparation of an amine as defined in claim 1, wherein the heterogeneous catalyst used is a crystalline oxide based on an aluminum phosphate and having faujasite structure and existing in the in the H form or ammonium form.

5. A process for the preparation of an amine as defined in claim 1, wherein the heterogeneous catalyst used is a crystalline oxide based on an aluminum phosphate and having faujasite structure and doped with one or more transition metals.

6. A process for the preparation of an amine as defined in claim 1, wherein the heterogeneous catalyst used is a crystalline oxide based on an aluminum phosphate and having faujasite structure and doped with one or more rare earth elements.

7. A process for the preparation of an amine as defined in claim 1, wherein the heterogeneous catalyst used is a crystalline oxide based on an aluminum phosphate and having faujasite structure and which has been doped with one or more elements selected from the group consisting of the alkali metals alkaline earth metals, or earth metals.

8. A process for the preparation of an amine as defined in claim 1, wherein the heterogeneous catalyst used is a crystalline oxide based on an aluminum phosphate and having faujasite structure and which has been shaped with a binding agent and calcined at temperatures ranging from 200° to 600° C.

9. A process for the preparation of an amine as defined in claim 1, wherein the heterogeneous catalyst used is a silicon-aluminum phosphate (SAPO), a metal-silicon-aluminum phosphate (MeAPSO), an aluminum phosphate (AlPO) containing aluminum in excess, or a metal-aluminum phosphate (MeAPO).

10. The process of claim 9, wherein the heterogeneous silicon-aluminum phosphate catalyst is SAPO-37 or HCAPO-37.

11. The process of claim 9, wherein the heterogeneous silicon-aluminum phosphate catalyst is MeAPSO-37.

12. The process of claim 9, wherein the heterogeneous catalyst is SAPO-37 or HCAPO-37.

13. The process of claim 9, wherein the heterogeneous catalyst is MeAPSO-37.

* * * * *